(12) United States Patent
Wellisz

(10) Patent No.: US 6,709,437 B2
(45) Date of Patent: *Mar. 23, 2004

(54) BONE ALIGNMENT AND FIXATION DEVICE AND INSTALLATION METHOD, USING BOWED STRUT ATTACHMENT STRUCTURE

(75) Inventor: Tadeusz Z. Wellisz, Los Angeles, CA (US)

(73) Assignee: Bioplate, Inc., Los Angeles, CA (US)

( * ) Notice: Subject to any disclaimer, the term of this patent is extended or adjusted under 35 U.S.C. 154(b) by 126 days.

This patent is subject to a terminal disclaimer.

(21) Appl. No.: 09/992,782

(22) Filed: Nov. 26, 2001

(65) Prior Publication Data

US 2003/0100899 A1 May 29, 2003

(51) Int. Cl.[7] .................................................. A61B 17/56
(52) U.S. Cl. ........................... 606/71; 606/69; 606/72; 606/77; 606/151
(58) Field of Search ............................ 606/69, 72, 53, 606/77, 70, 71, 73, 66, 67, 151

(56) References Cited

U.S. PATENT DOCUMENTS

| | | | |
|---|---|---|---|
| 4,936,844 A | 6/1990 | Chandler et al. | |
| 5,433,748 A * | 7/1995 | Wellisz | 623/10 |
| 5,674,222 A | 10/1997 | Berger et al. | |
| 5,810,822 A | 9/1998 | Mortier | |
| 5,868,746 A | 2/1999 | Sarver et al. | |
| 5,953,803 A | 9/1999 | Hahn | |
| 6,168,596 B1 * | 1/2001 | Wellisz et al. | 606/69 |
| 6,190,389 B1 * | 2/2001 | Wellisz et al. | 606/69 |
| 6,302,884 B1 * | 10/2001 | Wellisz et al. | 606/69 |
| 6,511,482 B1 * | 1/2003 | Wellisz et al. | 606/69 |
| 6,582,435 B2 * | 6/2003 | Wellisz et al. | 606/72 |
| 6,620,165 B2 * | 9/2003 | Wellisz | 606/69 |
| 2003/0100898 A1 * | 5/2003 | Wellisz | 606/69 |
| 2003/0100900 A1 * | 5/2003 | Wellisz | 606/72 |
| 2003/0100901 A1 * | 5/2003 | Wellisz et al. | 606/72 |
| 2003/0100902 A1 * | 5/2003 | Wellisz et al. | 606/72 |

* cited by examiner

Primary Examiner—Pedro Philogene
Assistant Examiner—David A Bonderer
(74) Attorney, Agent, or Firm—William W. Haefliger

(57) ABSTRACT

A clip to interconnect primary and secondary bone zones having edges, comprising in a first tab to extend over a surface of the secondary bone zone, above a level defined by that surface, and an extension of the tab projecting below the level, and a first projection carried by the extension for penetrating the primary bone zone below the first level, and the extension having bowed configuration, to enable forcible driving of the projection, to effect penetrating.

24 Claims, 4 Drawing Sheets

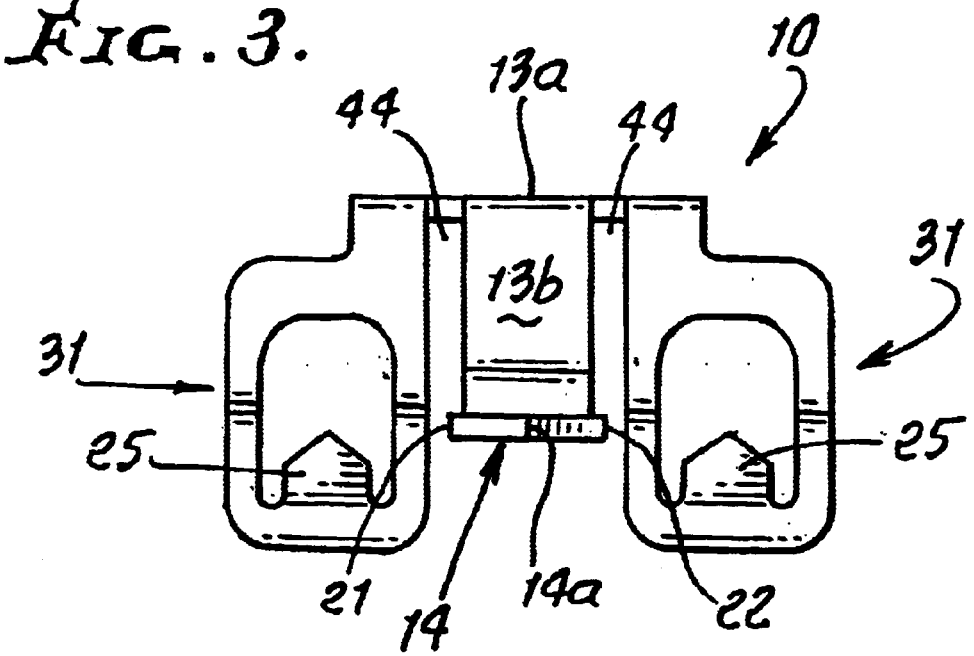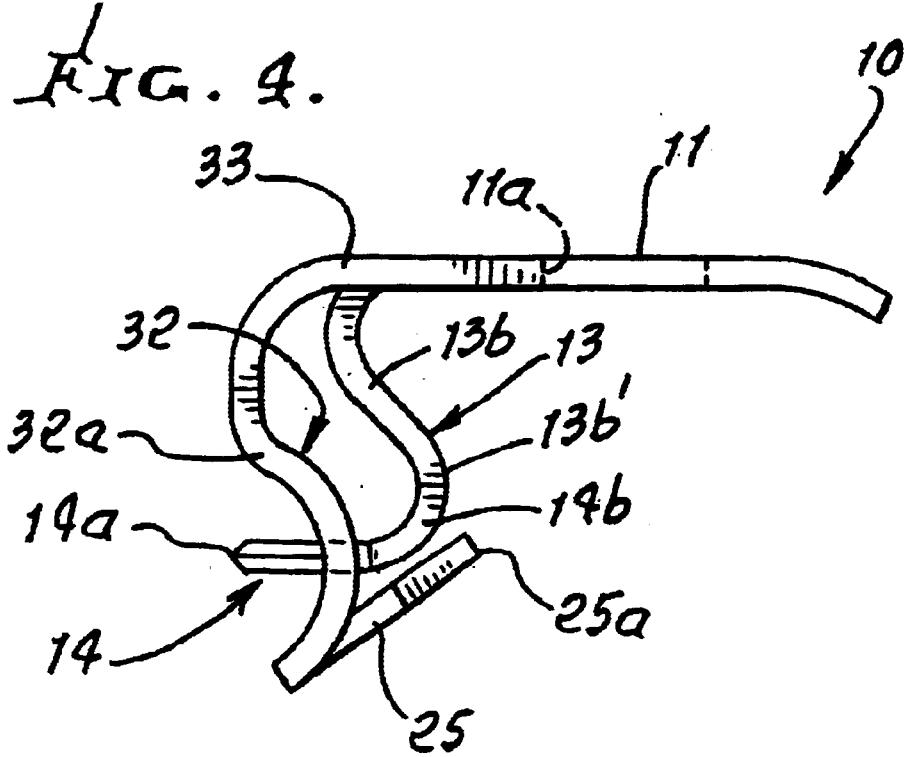

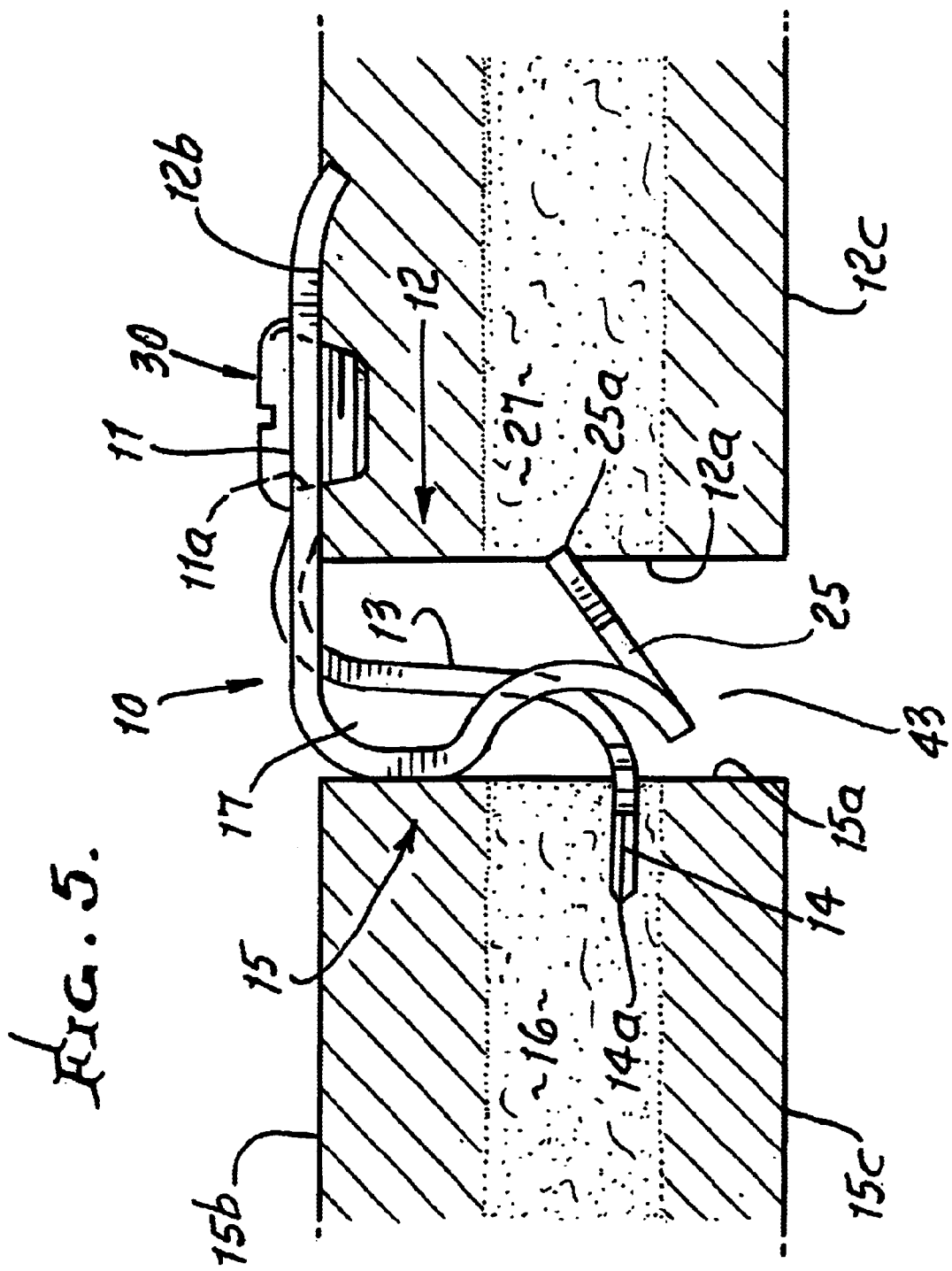

BONE ALIGNMENT AND FIXATION DEVICE AND INSTALLATION METHOD, USING BOWED STRUT ATTACHMENT STRUCTURE

BACKGROUND OF THE INVENTION

This invention relates generally to the alignment and fixation of bone segments as required for appropriate bone healing, for example after fracture or surgical intervention, and specifically to a device, and the tools needed to install the said device, for the alignment and fixation of cranial bone fragments.

In cases of bone fragmentation where bone fixation is desired, the appropriate alignment of the bone is also a desired result. This is especially true in the cranium, where bone fragmentation can occur as a result of trauma, congenital deformity, or of surgical intervention. In the field of neurosurgery, cranial bone fragments are frequently cut and removed to create defects to allow for access into the cranial cavity and the brain.

The bony cranium is generally regarded to have two surfaces: the outer surface which is characterized by the outer cortex of the bone and is adjacent to the scalp and soft tissue; and the inner surface which is characterized by the inner cortex of the bone and which is adjacent to the cranial cavity and the brain. Between the inner cortex and the outer cortex, which are dense layers of bone, lies the diploe which generally consists of soft bone and bone marrow. When a bone fragment is created, a cut between the bone fragment (the primary bone zone) and the remainder of the cranium (the secondary bone zone) is present.

Several methods of alignment and fixation of primary and secondary bone zones are known. Traditional techniques involve the use of several pieces of filament, such as wire, that are tied after being threaded through holes drilled obliquely through the outer cortex to the cut surface of both bone zones. Precise alignment of the two zones can be difficult and the technique can be cumbersome.

Commonly, the zones of bone can be aligned and fixated with a system of plates and screws (U.S. Pat. Nos. 5,372, 598; 5,413,577; and 5,578,036). A plate made of metal or other substance can be fixated to the outer cortex of the primary bone zone with screws whose penetration of the bone can be limited to the outer cortex. With three or more plates attached to the primary bone in such a way that the plates protrude beyond the edges of the primary bone zone, the primary bone zone can be introduced into a defect and aligned to the outer cortex of the secondary bone zone without danger of the primary bone zone falling too deeply into the defect in the secondary bone zone and exerting pressure on the underlying tissue such as the brain. Fixation can then be achieved by employing additional screws fixating the plates to the outer cortex of the secondary bone zone. Plates and screws systems allow for the alignment and fixation of the zones, while preventing the primary bone zone from falling below the level of the secondary bone zone without actually introducing a component of the device below the secondary bone zone. A plate with a spring clip extension has been described (U.S. Pat. No. 5,916,217). Plate and screw systems can be expensive and time consuming to use.

Devices that align the two bone zones by way of compressing them between the two disks positioned along the inner and outer cortex have been described. (Foreign Patents: DE 19603887C2, DE 19634699C1, DE 29812988U1, EP 0787466A1.) A pin connects the two disks aligning and securing two bone zones. These devices introduce foreign material that is left below the inner cortex, and they do not protect the underlying tissue from compression during the installation procedure.

Devices that fixate bone zones using friction forces created by a cam without a component that extends below the inner cortex are known and described (Patent DE 19634697C1). These devices also do not protect the brain from compression during the installation procedure.

Intramedulary pins are well known in the orthopedic fields for alignment of long bones. Such pins have also been described for cranial fixation (U.S. Pat. No. 5,501,685); however, the bone zones can not be aligned in three dimensions with this technique.

There is a need for an alignment and fixation device that is simple and rapid to use, versatile, and ultimately cost effective. There is also need for easily usable clip structure.

OBJECTS OF THE INVENTION

One object of the invention is to provide a device and instruments for its use and installation that aligns one cortex of a primary zone with one cortex of a secondary bone zone without extending to the opposing cortex, and which accurately fixates the bone zones to each other. When used in the field of neurosurgery, the device is applied to the primary bone zone and it aligns the outer cortex of the primary bone zone with the outer cortex of the secondary bone zone; it prevents the primary bone zone from entering the cranial cavity; and it provides fixation of the two bone zones.

One fixation feature of the invention relies on the principle that the device is fixated to the primary bone zone and the fixation feature grips the secondary bone zone by means of bowed strut elements engaging the soft areas of the medullary space, irregularities along the cut surface, or a slot cut into the cut surface of the secondary bone zone. Another feature is the use of a bowed strut or tab extension to support a projection or projections to be driven into the edge of a primary bone zone to retain the clip in anchored position.

SUMMARY OF THE INVENTION

The invention provides an improved clip meeting the above need or needs.

As will be seen, the preferred clip is configured to interconnect primary and secondary bone zones having edges spaced apart by a gap, the clip comprising a) a first tab to extend over a surface of the secondary bone zone, above a level defined by that surface, and b) an extension of the tab projecting below said level, and a first projection carried by the extension for penetrating the primary bone zone below said first level, c) said extension having bowed configuration, to enable forcible driving of the projection, to effect said penetrating.

The extension or strut may typically have S-shape to provide a spring carrying the first projection to be driven into bone tissue.

As will be seen, a second projection may be provided to be carried by the other tab, and configured to engage the secondary bone zone at the edge thereof.

In this regard, the second projection is typically to be located beneath the first tab; and the first projection is to be driven generally parallel to that tab and forwardly from a part of the bowed tab extension below tab level, and it preferably has a sharp terminal to enable penetration of diploe.

A further object is to provide the second projection to have a sharp terminal, and to extend at an acute angle toward the plane of the first tab, in order to resist removal relative to the secondary bone zone.

Yet another object is to provide another second projection carried by the tab in sidewardly spaced relation to the first mentioned second projection, and configured to engage the secondary bone zone at the edge thereof.

An additional object is to provide S-shaped spring support of both first and second projections, to enhance their functioning and assist their initial and subsequent positioning in the gap between the two bone zones. The positioning of the first projection supported independently of the second projection or projections, enables driving of the first projection without effecting the positioning and functioning of the second projection or projections.

An additional object is to provide a plate or flap defining the primary bone zone, and to provide multiple of the clips having their first projections penetrating the primary bone zone at different edges thereof, below a surface defined by the plate or flap.

The method of using the clip as referred to includes orienting the first projection to align with an edge of the primary bone zone and driving the first projection into the primary bone zone at the edge thereof, by driving said bowed extension which provides an anvil, and attaching the tab to said surface.

In this regard, the method may include effecting penetration of the edge of the secondary bone zone by a second projection in an angular direction toward the plane of the tab. The bowed or S-shapes of the independent supports for either or both the first and second projections provide enhanced spring effect, and aid in initial positioning of the projections, as well as their independent clip anchoring functions at multiple locations.

These and other objects and advantages of the invention, as well as the details of an illustrative embodiment, will be more fully understood from the following specification and drawings, in which:

DRAWING DESCRIPTION

FIG. 3 is a frontal view of the clip taken on lines 3—3 of FIG. 2;

FIG. 4 is a right side elevation taken on lines 4—4 of FIG. 2;

FIG. 5 is a view like FIG. 4, but showing use of the clip; and

DETAILED DESCRIPTION

Figure 6:
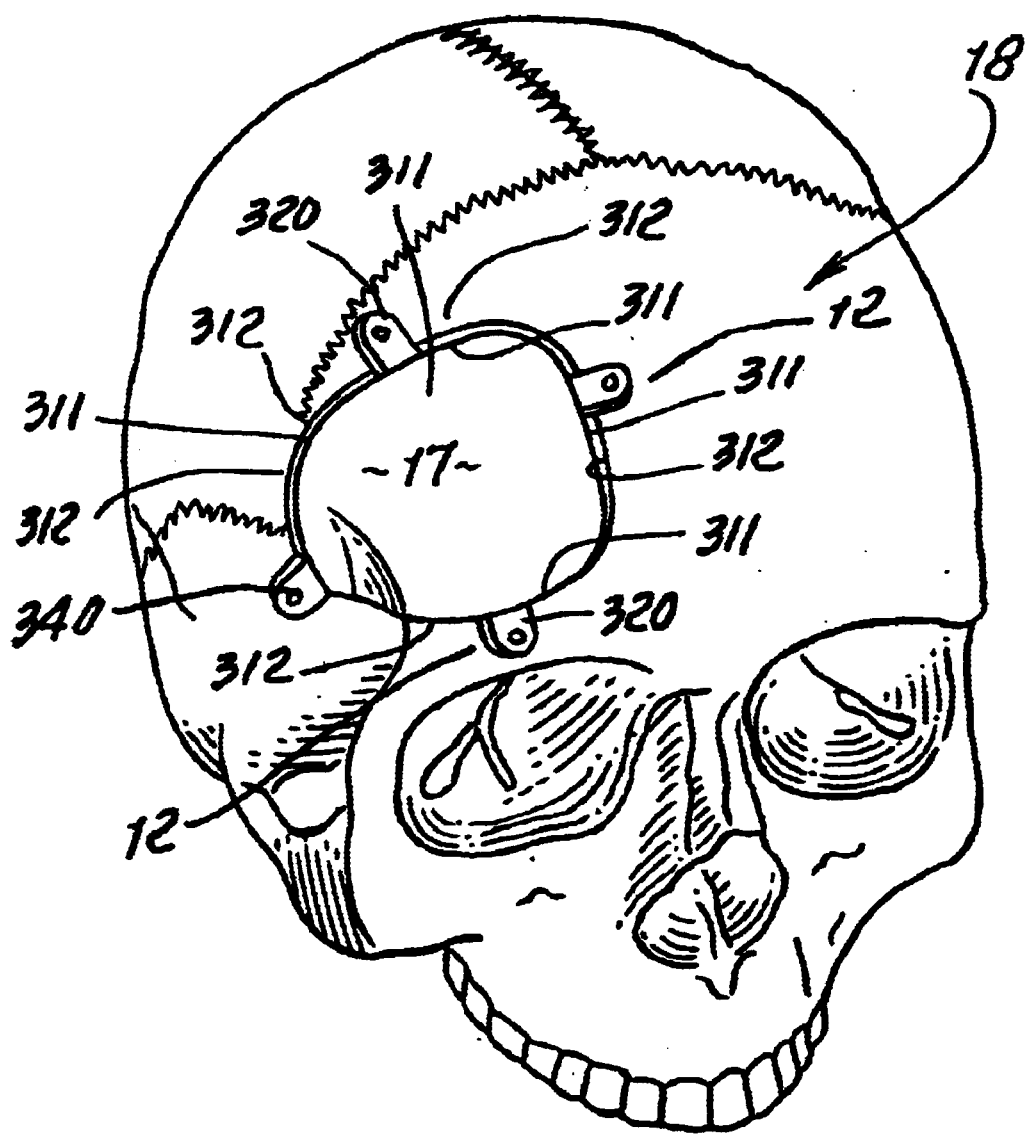
FIG. 6 is a perspective view showing a bone flap fixated on a skull, employing fixation clips.

Referring to FIGS. 5 and 6, the illustrated and preferred clip 10 is configured to interconnect primary and secondary bone zones 12 and 15 having opposed and spaced apart edges 15a and 12a. A cut or gap 43 is formed between the opposed edges of the primary and secondary bone zones. Diploe is shown at 16 between the top and bottom surfaces 15b and 15c of zone 15; and at 27 between the top and bottom surfaces 12b and 12c of zone 12. As also seen in FIG. 6, primary bone zone 15 may be defined by bone flap 17; and secondary bone zone or zones 12 may be defined by skull 18 and its zone extents at 12 opposing zones 15. In the adult, cranial bone or skull averages 7 mm in thickness, but varies between 3 and 12 mm.

Figure 1:
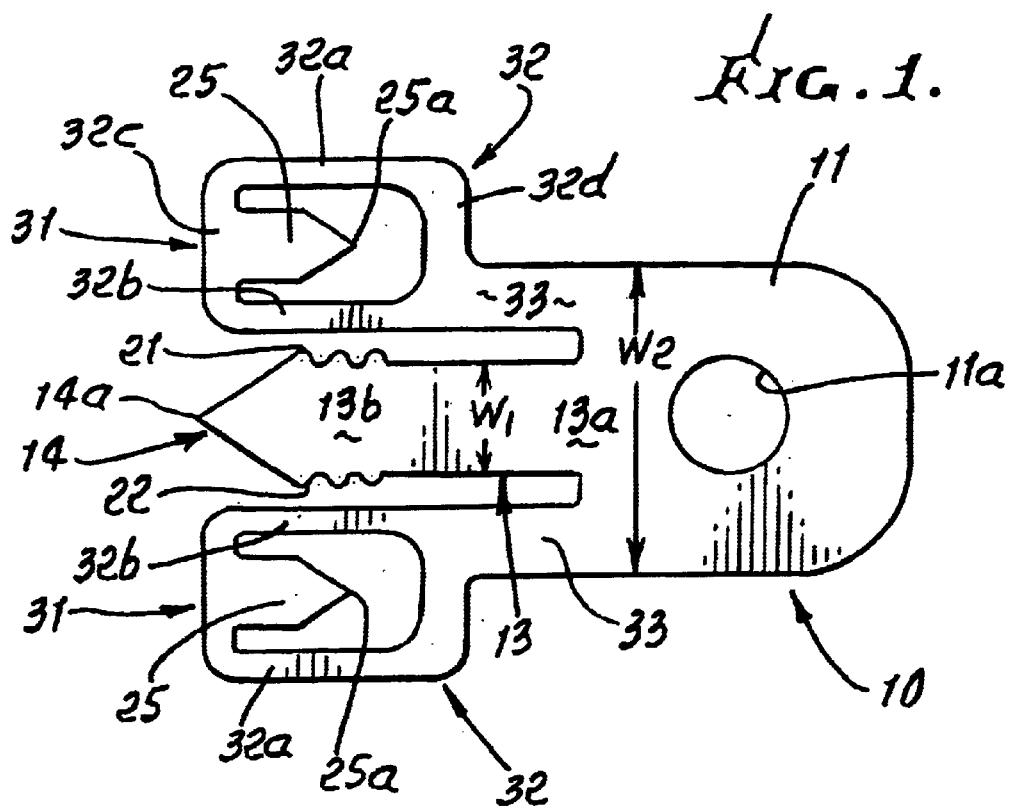
FIG. 1 is a plan view of a clip blank in one plane.
Figure 2:
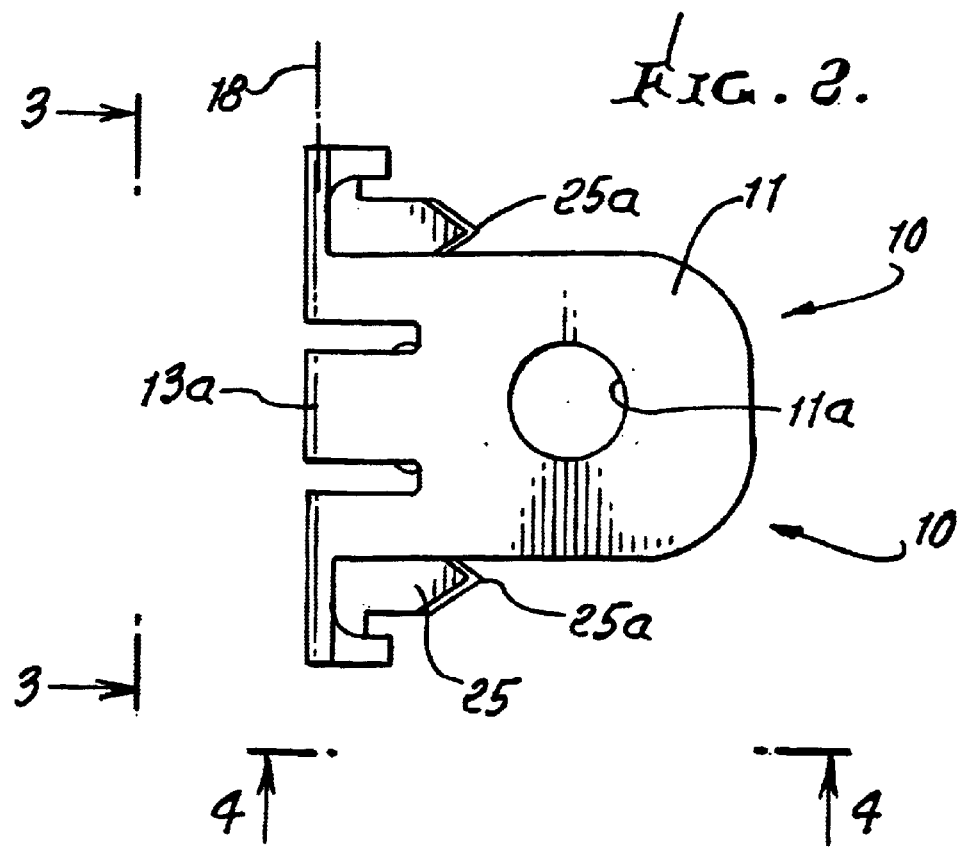
FIG. 2 is a top plan view of the formed or vent clip of FIG. 1.

The clip 10, is also shown in blank formed condition in FIG. 1, and in formed or folded condition in FIGS. 2–4. The clip, which is preferably metallic, includes the following:

a) a first tab 11 provided to extend over a surface 12b of secondary bone zone 12, and above a level defined by surface 12b, and b) a strut or extension 13 of tab 11 that projects below that level.

A first projection 14 is carried by the strut or extension 13, for penetrating the primary bone zone 15 at the edge 15a of that zone (and typically into diploe 16). See sharp terminal or tip portion 14a on the projection. Also, the strut or extension 13 has a bowed configuration, as for example an S-shape as seen in FIG. 4. That shape may act to yieldably urge, or position, the projection facing the bone zone edge 15a when inserted into the gap 17 between edge 15a of bone zone 15 and edge 12a of bone zone 12. If desired, the terminal 14a may be caused to yieldably engage edge 15a when inserted into gap 43 between 12a and 15a.

As is seen from FIGS. 1 and 2, the plate-like tab extension 13 is configured to be bent or folded as along a line 18 seen in FIG. 2, so that an upper part 13a of that extension remains in or approximate the plane of the tab 11, and so that bowed lower part 13b projects downwardly below that plane, below part 13a. Strut part 13a may be narrowed in width "$w_1$" relative to the width "$w_2$" of the tab, thereby isolating it from second projections 25 to be described. Projection 14 is curved at locus 14b to project forwardly, generally parallel to the plane of tab 11, as seen in FIG. 4. The rearwardly facing convex area 13b' of extension part 13b also provides an extended and stiffened driving or anvil area to receive driving force to effect penetration of the terminal 14a of the projection into diploe 16. The bowed configuration of part 13b may have S-shape, or near S-shape, as referred to, providing stiffening and spring action.

The first projection may have barb configuration, as may be provided by serrations 21 and 22, at opposed side edges of the projection, for retaining the first projection 14 in locked position when driven into diploe 16.

A second projection or projections are typically and preferably carried by tab 11, and configured to engage the secondary bone zone 12 at its edge 12a facing edge 15a, as seen in FIG. 5. Two such second projections 25 are shown in FIGS. 1–4, and are located at generally opposite sides of the first projection 14, and spaced from 14 at spaces 44, to isolate the grip functioning of projections 25 from the driving of projection 14. Accordingly, when fully installed in position as seen in FIG. 5, the clip is anchored to both bone zones 12 and 15. Projections 25, when formed or bent as shown in FIGS. 2–4, project in generally the opposite direction relative to the first projection 14. They also have sharp tapering terminals 25a to enable gouging or gripping penetration into diploe 27 exposed at edge 15a.

The projections 25 project at acute angles, rearwardly and upwardly toward the plane of the tab, to prevent clip retraction upwardly relative to the bone zones 12 and 15. In addition, the tab may be anchored to the secondary bone zone 12, as by a fastener 30, as shown in FIG. 5, received through opening 11a in the tab.

Referring back to FIGS. 1–4, attachment wings 31 are carried by the tab, the secondary projections being carried by the wings. Each wing is shown to include a ring-shaped extension 32 of a tab leg 33, the ring including arms 32a, 32b, 32c, and 32a that form a generally rectangular shape in the blank of FIG. 1. Arms 32a and 32b extend in generally parallel relation, and are bowed as seen in FIG. 4, having S-shape, and providing a spring-like and stiffened support for each projection 25, whereby the projections 25 are yieldably urged toward and into the diploe 27 as the clip is installed into FIG. 5 position.

The method of using the clip includes orienting the first projection 14 to align with an edge of the primary bone zone, and driving the first projection into the primary bone zone at the edge thereof, by driving said bowed extension at anvil 13b', and attaching the tab to said surface.

As described above, four pushed-in clips are seen in FIG. 6, the clips located in opposed pair positions, at four sides of the flap 17. Each tab 320 has a through hole 340 drilled or formed therein to receive a fastener such as a retention screw, indicated at 30 in FIG. 5, to penetrate and attach to the skull proximate the secondary bone regions.

The method preferably also includes displacing the clip in a direction (typically relatively downwardly toward the skull to bring 14a and 25a into gap 43 as seen in FIG. 5) to effect scraping of the edge 12a of the secondary bone zone 12 by the tip or tips 25a of the angled second projection or projections. Projection or projections 25 is or are oriented, i.e. angled, to resist displacement of the clip in an upward or opposite direction, relative to bone zone 12. For example, attempted upward and outward displacement would increase the "gouge-in" movement of the second projections, into the diploe 27.

Projections 14 and 25 can resiliently deflect, as by spring bending of their bowed support struts, to accommodate the clip to the gap 43 between 15 and 12, as during plate or tab downward installation. In FIG. 1, the lateral spacing of projections 14 and 25 further enhances clip installed stability.

The clips as referred to above are metallic, and preferably consist essentially of one of the following:
 i) titanium
 ii) titanium alloy
 iii) an alloy consisting essentially of titanium, aluminum and vanadium
 iv) an alloy consisting essentially of:
   about 90% by weight of titanium
   about 6% by weight of aluminum
   about 4% by weight of vanadium.

As also seen in FIG. 6 primary bone zones 311 may be defined by bone flap 17; and secondary bone zones 312 may be defined by skull 18 and its zone extents at 312 opposing zones 311. In the adult, cranial bone or skull averages 7 mm in thickness, but varies between 3 and 12 mm.

We claim:

1. A clip to interconnect primary and secondary bone zones having edges, comprising in combination:
   a) a first tab to extend over a surface of the secondary bone zone, above a level defined by that surface, and
   b) an extension of the tab projecting below said level, and a first projection carried by the extension for penetrating the primary bone zone below said first level,
   c) said extension having bowed configuration, to enable forcible driving of the projection, to effect said penetrating.

2. The combination of claim 1 wherein said first projection is in the form of a barb.

3. The combination of claim 1 wherein said extension has S-shape.

4. The combination of claim 1 wherein said projection has a tip portion projecting generally parallel to said tab.

5. The combination of claim 1 wherein said tab has the form of a plate that extends forwardly and then downwardly to define said extension.

6. The combination of claim 1 wherein said first projection has opposed edges that are serrated.

7. The combination of claim 1 including a second projection carried by the tab and configured to engage the secondary bone zone at the edge thereof, and below the level of the tab.

8. The combination of claim 7 wherein said second projection projects in generally the opposite direction relative to said first projection.

9. The combination of claim 7 wherein said second projection has a sharp terminal to enable penetrating of diploe.

10. The combination of claim 7 wherein said second projection extends at an acute angle toward the plane of the tab.

11. The combination of claim 7 including another second projection carried by the tab in sidewardly spaced relation to the first mentioned second projection, and configured to engage the secondary bone zone at the edge thereof, there being narrowed legs extending from the tab to ring-shaped supports for the second projections.

12. The combination of claim 11 wherein each said second projection has a sharp terminal to enable penetration of bone tissue.

13. The combination of claim 12 wherein said second projections are located generally at opposite sides of the first projection.

14. The combination of claim 7 including said primary bone zone penetrated by a tip of said first projection, and said secondary bone zone engaged by a tip of said second projection.

15. The combination of claim 7 including attachment wings which are carried by the tab and which carry said second projections.

16. The combination of claim 1 including a cranial bone flap defined by said primary bone zone.

17. The combination of claim 16 including multiple of said clips spaced peripherally about said flap.

18. The method of using a clip to interconnect primary and secondary bone zones having edges, the clip comprising
   a) a first tab to extend over a surface of the secondary bone zone, above a level defined by that surface, and
   b) a bowed extension of the tab projecting below said level, and a first projection carried by the extension for penetrating the primary bone zone below said first level,
   c) said method including orienting the first projection to align with an edge of the primary bone zone, and driving the first projection into the primary bone zone at the edge thereof, by driving said bowed extension,
   d) and attaching the tab to said surface.

19. The method of claim 18 including providing a second projection carried by the tab and configured to engage the secondary bone zone at the edge thereof, and below the level of the tab.

20. The method of claim 19 including providing for bowed spring support of the first projection.

21. The method of claim 20 including providing for bowed spring support of the second projection.

22. The method of claim 21 wherein said bowed spring supports have S-shape.

23. The method of claim 19 including providing for bowed spring support of the second projection.

24. The method of claim 21 including providing said first projection in the form of a barb.

* * * * *